United States Patent [19]

Hebgen et al.

[11] Patent Number: 5,175,382
[45] Date of Patent: Dec. 29, 1992

[54] PREPARATION OF 1,2-DICHLOROETHANE

[76] Inventors: Werner Hebgen, 20 Kurpfalzstrasse, 6907 Nussloch; Gerd Krome, 28 Am Wingertsberg, 6719 Weisenheim; Erhard Stahnecker, 36 Oberer Rainweg, 6900 Heidelberg, all of Fed. Rep. of Germany

[21] Appl. No.: 488,501

[22] Filed: Jan. 5, 1988

Related U.S. Application Data

[63] Continuation of Ser. No. 652,597, Sep. 20, 1984, abandoned.

[30] Foreign Application Priority Data

Sep. 22, 1983 [DE] Fed. Rep. of Germany ....... 3334225

[51] Int. Cl.$^5$ ............................................. C07C 17/34
[52] U.S. Cl. .................................... 570/221; 570/239; 570/219; 570/222; 570/223; 570/189; 570/245
[58] Field of Search ............... 570/221, 222, 189, 239, 570/219, 223

[56] References Cited

U.S. PATENT DOCUMENTS

| | | | |
|---|---|---|---|
| 2,474,206 | 6/1949 | de Nia | 260/656 |
| 3,444,252 | 5/1969 | Brown et al. | 570/224 |
| 3,446,586 | 5/1969 | Young | 23/154 |
| 3,453,340 | 7/1969 | Brown et al. | 570/224 |
| 3,642,921 | 2/1972 | McCarthy et al. | 570/243 |
| 4,035,473 | 7/1977 | Urioste et al. | 570/224 |
| 4,482,770 | 11/1984 | Schmidhammer et al. | 570/221 |

FOREIGN PATENT DOCUMENTS

| | | | |
|---|---|---|---|
| 511439 | 3/1955 | Canada | 570/243 |
| 0052271 | 10/1981 | European Pat. Off. | 570/243 |

Primary Examiner—Howard T. Mars
Assistant Examiner—Kimberly J. Kestler

[57] ABSTRACT 1,2-Dichloroethane is prepared by reacting ethylene, hydrogen chloride and oxygen or an oxygen-containing gas in the presence of a copper-containing catalyst by a process in which first hydrogen chloride and oxygen or an oxygen-containing gas are reacted in the presence of the catalyst, then ethylene is added, and the mixture is reacted in the presence of the said catalyst.

4 Claims, No Drawings

PREPARATION OF 1,2-DICHLOROETHANE

This application is a continuation of application Ser. No. 652,597, filed on Sep. 20, 1984, now abandoned.

The present invention relates to a process for the preparation of 1,2-dichloroethane by reacting ethylene, hydrogen chloride and oxygen or an oxygen-containing gas in the presence of a catalyst based on copper(II) chloride.

The preparation of 1,2-dichloroethane (EDC) is an intermediate step in the preparation of monomeric vinyl chloride. To do this, ethylene, hydrogen chloride and oxygen are generally reacted in stoichiometric amounts, the catalysts used containing copper(II) chloride as the active component. Oxygen is generally introduced in the form of air. Such processes are known as oxychlorination processes. In particular, two methods have become established in industry; in these methods, the catalyst is in the form of a fixed bed, or the reaction is carried out in a fluidized bed.

For the preparation of vinyl chloride, 1,2-dichloroethane is subjected to thermal cleavage, small amounts of byproducts being formed in addition to vinyl chloride, hydrogen chloride and uncleaved EDC. The byproducts include small amounts of acetylene, whose content increases in the hydrogen chloride stream obtained after the vinyl chloride and the other components have been separated off. The hydrogen chloride stream is then fed, together with ethylene and oxygen or an oxygen-containing gas, directly to the oxychlorination reaction over a copper(II) chloride catalyst. In this oxychlorination reaction, the acetylene leads to undesirable side reactions. Decomposition of the acetylene can result in the deposition of soot, thus reducing the selectivity and the activity of the catalyst. Moreover, in the oxychlorination reaction the acetylene is converted to chlorine-containing components which are difficult to remove from the 1,2-dichloroethane obtained. In the cleavage of 1,2-dichloroethane, these chlorine-containing components lead to derivatives which are troublesome in the vinyl chloride polymerization.

Processes have therefore been developed for the removal of the acetylene from the hydrogen chloride stream as obtained in the cleavage and the working up of the cleavage products. Thus, there are two basically different processes for removing acetylene from the hydrogen chloride obtained by thermal cleavage of 1,2-dichloroethane.

In one process, as disclosed in, for example, EP-A 1-0052271, the acetylene is hydrogenated with hydrogen, using a supported platinum or palladium catalyst, a mixture of ethylene and ethane being formed. The disadvantages of this process are that, in addition to ethylene, ethane is formed, which is undesirable for further processing, snd the use of hydrogen is uneconomical and entails technical problems with regard to safety.

In another process, as disclosed in, for example, U.S. Pat. No. 2,474,206, the cleavage products obtained from 1,2-dichloroethane are separated into a product stream which is free of acetylene, and another product stream which contains mainly hydrogen chloride and vinyl chloride in addition to the acetylene. Further acetylene is added to this product stream, and the resulting stream is passed over a catalyst, the acetylene reacting with the hydrogen chloride in a hydrochlorination reaction and being virtually completely converted to vinyl chloride.

These processes have the disadvantages that the relatively expensive compound acetylene is added, and the problem of the volatility of the hydrochlorination catalysts has not yet been completely solved. According to U.S. Pat. No. 3,446,586, the stream which is obtained after the cleavage of 1,2-dichloroethane and preferably contains hydrogen chloride in addition to acetylene can, after removal of the other components, be brought into contact with anhydrous $AlCl_3$. In this procedure, acetylene is preferentially converted to ethyl chloride and 1,1dichloroethane (which are undesirable in the preparation of vinyl chloride). These conventional processes are therefore not completely satisfactory.

It is an object of the present invention to provide a process for the preparation of 1,2-dichloroethane by reacting ethylene, hydrogen chloride and oxygen or an oxygen-containing gas in the presence of a catalyst based on cooper(II) chloride, in which the acetylene present in small amounts in the hydrogen chloride is converted so that the resulting reaction products do not present problems in the subsequent oxychlorination reaction.

We have found that this object is achieved, in accordance with the invention, by a process for the preparation of 1,2-dichloroethane by reacting ethylene, hydrogen chloride and oxygen or an oxygen-containing gas in the presence of a catalyst containing copper(II) chloride, in which first hydrogen chloride and oxygen or an oxygen-containing gas are brought into contact in the presence of the said catalyst, then ethylene is admixed, and the mixture is subjected to the oxychlorination reaction in the presence of the said catalyst.

Compared with the conventional processes, this process has the advantage that additional starting materials, such as hydrogen or acetylene, are not required, nor is it necessary to use a catalyst which is not employed in the oxychlorination reaction. We have found that the small amounts of acetylene react with hydrogen chloride in the presence of oxygen or of an oxygen-containing gas preferentially to give trans- and cis-dichloroethylene and 1,1,2-trichloroethane. These products do not interfere in the subsequent oxychlorination reaction and can be readily removed from the 1,2-dichloroethane obtained. The process according to the invention is carried out in other respects by the industrial procedures conventionally used for oxychlorination reactions.

The reactants, i.e. ethylene, hydrogen chloride and oxygen or an oxygen-containing gas, are fed to the mixing system, advantageously in stoichiometric amounts, i.e. the said reactants are mixed in a ratio such that there are about 2 moles of ethylene and about 4 moles of hydrogen chloride per mole of oxygen. The amounts can vary by $\pm 10\%$ from the stated molar amounts. Hence, in the novel process, hydrogen chloride and oxygen or an oxygen-containing gas are first mixed in the presence of the catalyst containing copper chloride, so that the gas streams are brought into contact with one another and react over the catalyst. The reaction conditions are the same as those conventionally employed in the oxychlorination reaction, which will be described below. The residence time for this reaction is advantageously chosen as from 3 to 30 seconds. These procedures involving mixing and bringing into contact with the catalyst containing copper(II) chloride can be carried out in a prereactor or directly in the oxychlorination reactor; in the latter case, the ethylene is first added at a remote point in the product stream. Advantageously, oxygen is introduced into the oxychlorination reactor not in pure form but together with inert gases, for example as air, since the presence of the nitrogen or of the inert gases does not interfere with the reaction but is advantageous with regard to temperature control.

When the reaction of the hydrogen chloride containing a small amount of acetylene with the oxygen stream is complete, a stoichiometric amount of ethylene is added to the mixture. If the reaction has been carried out in a prereactor, the mixture is then fed to the oxychlorination reactor. If the reaction of the acetylene-containing hydrogen chloride stream with the oxygen has been carried out in the oxychlorination reactor, ethylene is then admixed.

The oxychlorination reaction can then be carried out by a conventional procedure, a fluidized bed or a fixed bed method being used. In the fixed bed method, a procedure in which the reactants are reacted in only one reaction zone has proven useful. If a fixed-bed reactor is employed, the reaction is advantageously carried out under from 2 to 6 bar, the pressure at the beginning of the reaction zone being from 4 to 6 bar, and that at the end of the reaction zone being from 2 to 4 bar. Advantageously, the reaction takes place at from 180° to 350° C., advantageously from 230° to 290° C.

If the fluidized-bed method is employed, the reaction temperature is from 220° to 370° C., advantageously from 220° to 260° C., and the reaction is carried out under an absolute pressure of from 1 to 10, preferably from 4 to 9, bar. The pressure and the temperature must be chosen so that the dew point is exceeded everywhere in the reactor. The residence time is about 5–40 seconds.

If a fixed bed is employed, the catalyst used is a supported copper(II) chloride catalyst, as conventionally used for oxychlorination. The carrier used is advantageously $Al_2O_3$. These catalysts contain from 1 to 12% by weight, based on the carrier, of copper(II) chloride. The catalyst particles are advantageously cylindrical or annular, the diameter and the height both being from 3 to 10 mm. In the case of the rings, the internal diameter is from 2 to 5 mm. The catalyst advantageously has a bulk density of from 0.5 to 0.8 kg/liter. In a particularly advantageous procedure, a less active catalyst, i.e. one which contains about 1.0–4.0% by weight, based on the amount of catalyst, of copper, is placed at the beginning of the reaction zone, and a more active catalyst, i.e. one which contains about 7–12% by weight, based on the catalyst material, of copper, is placed at the end of the reaction zone. The catalysts are introduced in bulk into the reactor, so that the above bulk density results.

If a fluidized bed is employed, the most advantageously used catalyst is one which consists of particles of from 20 to 400 μm and is abrasion-resistant. The amount of copper is from 3 to 12, preferably from 3.5 to 7.0, % by weight. Too high a copper content does not improve the reaction rate and results in the catalyst tending to cake in the reactor.

In the fixed-bed and fluidized-bed methods, it is also possible to use silicates and mixtures of aluminum oxides and silicon oxides as carriers. The specific surface area is from 40 to 400 m²/g. The preparation of the catalysts and the improvement of the selectivity and reduction of the volatility of the copper by admixing chlorides or oxides of alkali metals, alkaline earth metals and rare earth metals are known to the skilled worker.

The products are then removed from the reaction zone and are worked up in a conventional manner, i.e. 1,2-dichloroethane and water are first removed by condensation, and the non-condensable components, i.e. the waste gases, are either fed via waste gas washers or adsorbers in order to retain chlorohydrocarbons and unreacted ethylene, or are fed to an incineration plant, in which the chlorohydrocarbons and any ethylene present undergo complete combustion. The resulting hydrogen chloride can be recovered, for example via a water wash and subsequent distillation, and can be employed in the oxychlorination.

The Examples which follow illustrate the invention.

EXAMPLES 1 TO 4

1. A 3 m long steam-heated double-walled tube having an internal diameter of 50 mm was charged with an oxychlorination catalyst in the form of 5×5 mm tablets consisting of aluminum oxide with 9.0% by weight of Cu and 1.0% by weight of K.

The reactor, the feed line and the outlet line were heated with steam under 16 bar. 1.98 kg/hour of HCl and 1.96 kg/hour of air were mixed, and the mixture was fed via this prereactor. This corresponds to a space velocity of 0.89 kg of gas per kg of catalyst per hour, and a residence time of 19.8 s. The temperature upstream from the reactor was 147° C., and that at the reactor outlet was 164° C. The analyses of the HCl/air mixture are shown in Table 1.

2. The prereactor described in Example 1 was only half filled with catalyst, and was operated using the same amounts as in Example 1. The space velocity was 1.78 kg of gas per kg of catalyst per hour, the residence time was 9.9 s and the temperature upstream from the reactor was 133° C. and that downstream from the reactor was 155° C. The analyses are summarized in Table 1.

3. The reactor described in Example 2 was operated using 1 kg/hour of air and 1 kg/hour of HCl, corresponding to a space velocity of 0.9 kg of gas per kg of catalyst per hour and a residence time of 19.5 s. The temperature upstream from the reactor was 123° C. and that downstream from the reactor was 148° C. The analyses are shown in Table 1.

4. The reactor described in Example 2 was once again used, and 3 kg/hour of air and 3 kg/hour of HCl were fed in. This corresponds to a space velocity of 2.72 kg of gas per kg of catalyst per hour and a residence time of 6.5 s. The temperature upstream from the reactor was 146° C., and that downstream from the reactor was 162° C. The analyses are shown in Table 1.

The reaction mixtures obtained as described in Examples 1 to 4 can then be mixed with a stoichiometric amount of ethylene, and the mixture fed to an oxychlorination reactor. We found that no deposits were formed on the catalyst, even after prolonged operation of the reactor.

EXAMPLE 5

Table 2 compares analyses of the condensation product obtained with and without operation of the prereactor. It can be seen that the purity of the 1,2-dichloroethane is virtually unchanged, and the content of the components formed in the prereactor is not at all higher, but also virtually the same. On the other hand, significant differences are found with regard to trichloroethylene, tetrachloroethylene, tetrachloroethane and pentachloroethane. In particular, the substantially lower content of trichloroethylene is advantageous with respect to the subsequent working up of 1,2-dichloroethane by distillation.

ride in admixture with various by-products including hydrogen chloride and small quantities of acetylene

TABLE 1

| Values in vol. ppm | Example 1 | | Example 2 | | Example 3 | | Example 4 | |
|---|---|---|---|---|---|---|---|---|
| | Upstream from the reactor | Downstream from the reactor | Upstream from the reactor | Downstream from the reactor | Upstream from the reactor | Downstream from the reactor | Upstream from the reactor | Downstream from the reactor |
| Ethylene | 350 | 11 | 310 | 54 | 282 | 9 | 433 | 158 |
| Acetylene | 896 | 1 | 909 | 3 | 788 | 3 | 1,124 | 3 |
| Vinyl chloride | 80 | 2 | 7 | 12 | 92 | 3 | 105 | 48 |
| Ethyl chloride | 1 | 5 | 1 | 7 | 2 | 12 | 1 | 9 |
| Vinylidene chloride | 10 | — | — | — | — | — | — | — |
| trans-Dichloroethylene | 6 | 123 | 7 | 426 | 7 | 273 | 149 | 422 |
| $CCl_4$ | — | — | — | — | — | — | — | — |
| 1,1-Dichloroethane | — | — | 3 | 1 | 5 | 1 | 10 | 3 |
| cis-Dichloroethylene | 1 | 42 | 2 | 143 | 1 | 137 | 2 | 200 |
| Benzene | — | — | — | — | — | — | — | — |
| Trichloroethylene | — | — | — | — | — | — | — | — |
| $CHCl_3$ | — | — | — | — | — | — | 2 | — |
| 1,2-Dichloroethane | 1,139 | 2,053 | 973 | 1,221 | 639 | 1,628 | 1,118 | 1,459 |
| Unknown | 9 | 30 | — | 7 | — | 7 | — | 10 |
| 1,1,2-Trichloroethane | — | 21 | — | 47 | — | 177 | — | 118 |
| 1,1,2,2-Tetrachloroethane | — | — | — | — | — | — | — | — |

TABLE 2

Analysis of crude EDC after the oxichlorination reaction

| Values in % by weight | Examples 1 to 4 with prereactor | Example 5 without prereactor |
|---|---|---|
| Ethylene | 0.001 | 0.002 |
| Vinyl chloride | 0.001 | 0.001 |
| Ethyl chloride | 0.101 | 0.097 |
| Vinylidene chloride | — | — |
| trans-Dichloroethylene | 0.037 | 0.061 |
| 1,1-Dichloroethane | 0.008 | 0.007 |
| $CCl_4$ | 0.109 | 0.092 |
| cis-Dichloroethylene | 0.045 | 0.051 |
| $CHCl_3$ | 0.044 | 0.041 |
| Trichloroethylene | 0.015 | 0.126 |
| 1,2-Dichloroethane | 98.793 | 98.818 |
| Chloral | 0.076 | 0.072 |
| Tetrachloroethylene | 0.003 | 0.061 |
| Chlorobromoethane | 0.003 | 0.005 |
| 1,1,2-Trichloroethane | 0.420 | 0.421 |
| 1,1,1,2-Tetrachloroethane | — | 0.001 |
| 1,1,2,2-Tetrachloroethane | 0.339 | 0.113 |
| Pentachloroethane | 0.005 | 0.031 |

We claim:

1. In a process wherein ethylene, hydrogen chloride and oxygen or an oxygen-containing gas are introduced into an oxychlorination reactor and caused to react in the presence of a copper-based catalyst to produce 1,2-dichloroethane as an intermediate, which compound is then thermally cleaved to obtain vinyl chloride as the ultimate product, said cleavage producing vinyl chloride in admixture with various by-products including hydrogen chloride and small quantities of acetylene which concentrates and remains in the hydrogen chloride stream after the vinyl chloride and other components of the mixture are separated therefrom, the separated acetylene-containing hydrogen chloride stream then being recycled directly to the oxychlorination reactor to provide the hydrogen chloride reactant, the improvement in said process comprising:

first, feeding the acetylene-containing hydrogen chloride stream into a pre-reactor wherein the deleterious acetylene component is essentially converted to the harmless compounds dichloroethylene and 1,1,2-trichloroethane by reaction with oxygen or an oxygen-containing gas in the presence of a copper-based catalyst, and thereafter passing the now acetylene-free hydrogen chloride stream to said oxychlorination reactor for reaction with ethylene and oxygen.

2. The process of claim 1, wherein the residence time in said pre-reactor is from 3 to 30 seconds.

3. The process of claim 1, wherein said copper-based catalyst in both the pre-reactor and oxychlorination reactor is a copper (II) chloride catalyst.

4. The process of claim 1, wherein said copper-based catalyst in both the pre-reactor and oxychlorination reactor is copper(II) chloride on $Al_2O_3$ as the carrier containing 1 to 12% by weight copper(II) chloride and 0 to 1% by weight potassium, based on the carrier.

* * * * *